United States Patent
Shibahara et al.

(10) Patent No.: US 9,589,344 B2
(45) Date of Patent: Mar. 7, 2017

(54) VOLUME DATA ANALYSIS SYSTEM AND METHOD THEREFOR

(71) Applicant: Hitachi, Ltd., Tokyo (JP)

(72) Inventors: Takuma Shibahara, Tokyo (JP); Takafumi Koike, Tokyo (JP)

(73) Assignee: Hitachi, Ltd., Tokyo (JP)

(*) Notice: Subject to any disclaimer, the term of this patent is extended or adjusted under 35 U.S.C. 154(b) by 93 days.

(21) Appl. No.: 14/655,512

(22) PCT Filed: Dec. 28, 2012

(86) PCT No.: PCT/JP2012/084207
§ 371 (c)(1),
(2) Date: Sep. 10, 2015

(87) PCT Pub. No.: WO2014/103061
PCT Pub. Date: Jul. 3, 2014

(65) Prior Publication Data
US 2016/0005167 A1  Jan. 7, 2016

(51) Int. Cl.
*G06T 7/00* (2006.01)
*A61B 8/08* (2006.01)
(Continued)

(52) U.S. Cl.
CPC ............ *G06T 7/0012* (2013.01); *A61B 5/055* (2013.01); *A61B 6/5211* (2013.01);
(Continued)

(58) Field of Classification Search
None
See application file for complete search history.

(56) References Cited

U.S. PATENT DOCUMENTS

| | | | |
|---|---|---|---|
| 7,184,814 B2* | 2/2007 | Lang | A61B 5/055 324/307 |
| 7,239,908 B1* | 7/2007 | Alexander | A61B 5/055 378/21 |

(Continued)

FOREIGN PATENT DOCUMENTS

| | | |
|---|---|---|
| JP | 2009-22342 A | 2/2009 |
| JP | 4388121 B2 | 10/2009 |

(Continued)

OTHER PUBLICATIONS

Andras Kelemen et al., Three-dimensional Model-based Segmentation of Brain MRI, Proceedings of the IEEE Workshop on Biomedical Image Analysis, IEEE Computer Society Press, 1998, pp. 4-13.

(Continued)

*Primary Examiner* — Tsung-Yin Tsai
(74) *Attorney, Agent, or Firm* — Mattingly & Malur, PC (57) ABSTRACT

A controller has a function that: poygonizes and converts three-dimensional volume data, which is generated by a modality, into polygon data; divides this polygon data into a plurality of clusters; calculates an L2 norm vector of spherical harmonics as a feature vector with respect to each of the clusters based on the polygon data constituting each cluster; identifies whether each cluster is a target or not, based on each calculated feature vector and learning data; and displays an image of a cluster identified as the target at least on a screen.

10 Claims, 9 Drawing Sheets

(51) Int. Cl.
  *G01S 15/89* (2006.01)
  *A61B 5/055* (2006.01)
  *G06T 15/08* (2011.01)
  *G06T 17/20* (2006.01)
  *A61B 6/03* (2006.01)
  *A61B 6/00* (2006.01)
  *A61B 8/00* (2006.01)
  *G01S 7/52* (2006.01)

(52) U.S. Cl.
  CPC .......... *A61B 6/5217* (2013.01); *A61B 6/5247* (2013.01); *A61B 8/483* (2013.01); *G01S 15/8993* (2013.01); *G06T 15/08* (2013.01); *G06T 17/20* (2013.01); *A61B 6/032* (2013.01); *A61B 6/037* (2013.01); *A61B 6/466* (2013.01); *A61B 8/466* (2013.01); *A61B 8/5223* (2013.01); *G01S 7/52036* (2013.01); *G06T 2207/10072* (2013.01); *G06T 2207/10081* (2013.01); *G06T 2207/20148* (2013.01); *G06T 2207/30056* (2013.01); *G06T 2210/41* (2013.01)

(56) References Cited

U.S. PATENT DOCUMENTS

| | | | |
|---|---|---|---|
| 2005/0089878 A1* | 4/2005 | Debe | G06F 19/18 435/6.14 |
| 2007/0165924 A1* | 7/2007 | Nicponski | G06T 7/0012 382/128 |
| 2009/0024029 A1 | 1/2009 | Murashita | |
| 2012/0063655 A1* | 3/2012 | Dean | G06F 19/321 382/128 |
| 2012/0256915 A1* | 10/2012 | Jenkins | G06T 15/40 345/419 |

FOREIGN PATENT DOCUMENTS

| | | |
|---|---|---|
| WO | 2005/052860 A2 | 6/2005 |
| WO | 2006/044242 A2 | 4/2006 |
| WO | 2007/035340 A2 | 3/2007 |

OTHER PUBLICATIONS

International Search Report of PCT/JP2012/084207.

* cited by examiner

VOLUME DATA ANALYSIS SYSTEM AND METHOD THEREFOR

TECHNICAL FIELD

The present invention relates to a volume data analysis system and method for extracting an object from three-dimensional volume data.

BACKGROUND ART

A medical image processing unit that visualizes information about the inside of a human body has been being rapidly widespread in the medical field and is used for various diagnoses. Examples of modalities used for the medical image processing unit are X-ray CT (Computed Tomography), PET (Positron Emission Tomography), MRI (Magnetic Resonance Imaging) and US (Ultrasonography), and these modalities can obtain three-dimensional volume data.

Doctors can diagnose the presence or absence of a liver cancer and progression of the cancer by using the X-ray CT as a modality and visualizing volume data of the liver, which is acquired by the X-ray CT, as an image.

Furthermore, in recent years the development of an automatic detector (hereinafter sometimes referred to as "CAD" [Computer Aided Diagnosis]) that automatically detects diseases represented by, for example, cancers from the volume data has been promoted for the purpose of reducing burdens on doctors. However, since the inside of a human body has very complicated structures, there may be errors in detection results acquired by using the automatic detector. Furthermore, noises peculiar to certain modalities may be mixed in the volume data depending on the modalities and some noises make it difficult for the automatic detector to automatically detect the diseases. Therefore, currently there is a strong demand for the development of an automatic detector capable of detecting the diseases as correctly as the doctors would detect. It should be noted that the technique detecting an object from the volume data is disclosed in, for example, PTL 1 and PTL 2 below.

CITATION LIST

Patent Literature

[PTL 1] Japanese Patent Application Laid-Open (Kokai) Publication No. 2009-22342
[PTL 2] U.S. Pat. No. 4,388,121

SUMMARY OF INVENTION

Problems to be Solved by the Invention

According to PTL 1, threshold processing for determining the size of an object according to a threshold is executed when extracting the object from the volume data, so that noise components included in the volume data can be eliminated. However, if the object exists in a non-noise area, but its size is equal to or less than a threshold, there is a problem of the possibility that the object may be eliminated. Also, the manipulation to set the threshold is cumbersome and doctors and engineers (hereinafter referred to as the "user(s)") who use the device bear heavy burdens. Furthermore, the threshold needs to be set for each of different types of measures.

According to PTL 2, a feature quantity with which polypus detection is conducted has three-dimensional rotary dependency, so that it is necessary to perform learning for each different rotation. Specifically speaking, when rotary patterns are not increased, there is a possibility that detection performance may degrade. Also, there are concerns for an increase in a calculation cost required for pattern rotations. Furthermore, since it is necessary to calculate the feather quantity directly from a voxel value of three-dimensional volume data, the calculation cost is large.

The present invention was devised in light of the above-described problems of the prior art technology and it is an object of the invention to provide a volume data analysis system and method capable of reducing the calculation cost.

Means for Solving the Problems

In order to solve the above-described problem, the present invention is characterized in that: three-dimensional volume data generated by a modality is polygonized and converted into polygon data; the converted polygon data is divided into a plurality of clusters; an L2 norm vector of spherical harmonics is calculated as a feature vector with respect to each of the clusters based on the polygon data constituting each cluster; whether each cluster is a target or not is identified based on each calculated feature vector and learning data acquired by machine learning by using training data; and at least an image of a cluster identified as the target is displayed on a screen.

Advantageous Effects of Invention

The calculation cost can be reduced according to the present invention.

MODE FOR CARRYING OUT THE INVENTION

Embodiment

Figure 1:
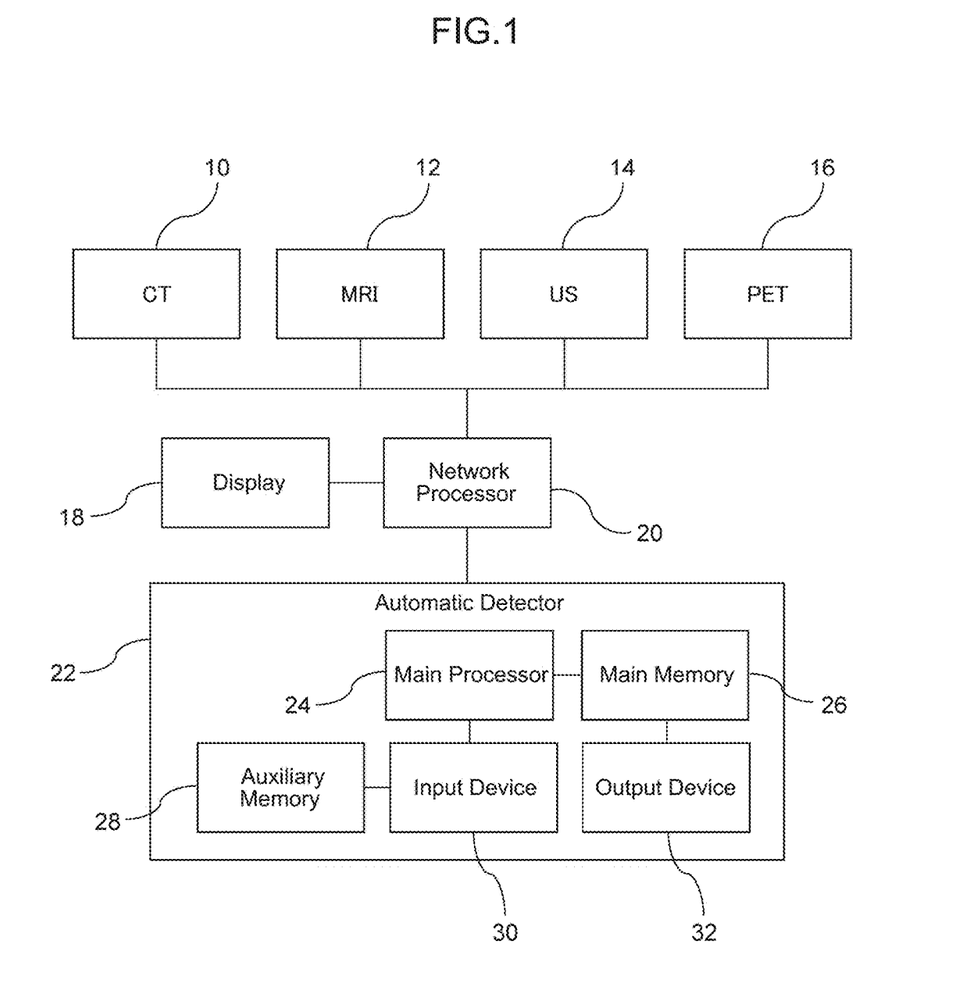
FIG. 1 is a configuration diagram of a volume data analysis system.

An embodiment of the present invention will be explained below with reference to drawings. FIG. 1 is a configuration diagram of a volume data analysis system. Referring to FIG. 1, the volume data analysis system includes a plurality of modalities 10, 12, 14, 16, a display 18, a network processor 20, and an automatic detector 22 and can automatically analyze diseases such as a cancer from volume data. Each modality 10 to 16 is connected to the network processor 20 and the network processor 20 is connected to the display 18 and the automatic detector 22.

The automatic detector 22 is configured of a main processor 24, a main memory 26, an auxiliary memory 28, an input device 30, and an output device 32. The main processor 24 is connected to the network processor 20, is also connected via the main memory 26 to the output device 32, and is further connected via the input device 30 to the auxiliary memory 28.

Each modality 10 to 16 is configured as a detector that transmits and receives signals to and from an analysis object or measuring object and generates three-dimensional volume data about the object (hereinafter sometimes referred to as the target). Under this circumstance, the modality 10 is configured of a X-ray CT, the modality 12 is configured of MRI, the modality 14 is configured of US, and the modality 16 is configured of PET.

Generally, when the target is a fetus, the modality (US) 14 is used among the modalities 10 to 16 in order to avoid the influence of exposures; and if the target is the focus of disease such as a cancer, the modality (X-ray CT) 10, the modality (MRI) 12, or the modality (PET) 16 is used in order to acquire precise volume data.

Regarding this embodiment, an explanation will be given about an example in which the three-dimensional volume data acquired from the modality 14 is processed in order to use the fetus as a measuring object or an analysis object.

The modality 14 has a function that scans a fault plane (scan plane) inside the fetus with ultrasonic waves from, for example, an ultrasonic probe, receives and digitalizes a reflection echo signal returned from each site of biological tissues of the fault plane, processes the digitalized data as frame data of the fault plane, and also generates the frame data (volume data of each tomographic image) acquired by scanning a plurality of scan planes as three-dimensional volume data. In other words, the modality 14 has a function that generates the three-dimensional volume data by receiving the reflection echo signal (measured signal) acquired by scanning the measuring object.

The three-dimensional volume data generated by the modality 14 is transferred to the main processor 24 via the network processor 20. Under this circumstance, the three-dimensional volume data is stored as a cubic three-dimensional array, for example, as a voxel value of 512×512×512 voxels (a value corresponding to a luminance value of a two-dimensional image) in the main memory 26.

The main processor 24 executes processing for generating image data image data (for example, image data with respect to a three-dimensional image acquired by projecting a three-dimensional shape, which is determined based on the value of the three-dimensional volume data, onto a two-dimensional plane) from the received three-dimensional volume data, transfers the generated image data to the display 18 via the network processor 20, and displays the three-dimensional image of the transferred image data on a screen of the display 18.

The display 18 is a display device having a touch panel function, is configured as a display device for displaying processing results of the main processor 24, and has a function as an input device for inputting information such as correction information in response to the user's manipulation such as correction manipulation.

The network processor 20 transmits and receives data or information to and from each of the modalities 10 to 16, transmits and receives data or information to and from the display 18, and further transmits and receives data or information to and from the main processor 24.

The automatic detector 22 is configured as a general medical workstation. The main processor 24 includes, for example, a CPU (Central Processing Unit) and functions as a controller that supervises and controls the entire automatic detector 22. Under this circumstance, the main processor 24 also functions as a controller that processes the three-dimensional volume data generated by the modality 14 and information input from the display 18 and the input device 30.

The main memory 26 is composed of, for example, a DRAM (Dynamic Random Access Memory) and is configured as a storage device that stores, for example, the three-dimensional volume data. The auxiliary memory 28 is composed of, for example, SSDs (Solid State Drives) and is configured as an auxiliary storage device. The input device 30 is composed of, for example, a mouse, a track ball, and a keyboard and has a function that accepts instructions from the user. The output device 32 is composed of, for example, a DVD (Digital Versatile Disc)-RW (ReWritable) drive. Incidentally, the input device 30 can be used as an input device for inputting the correction information operated by the user.

Figure 2:
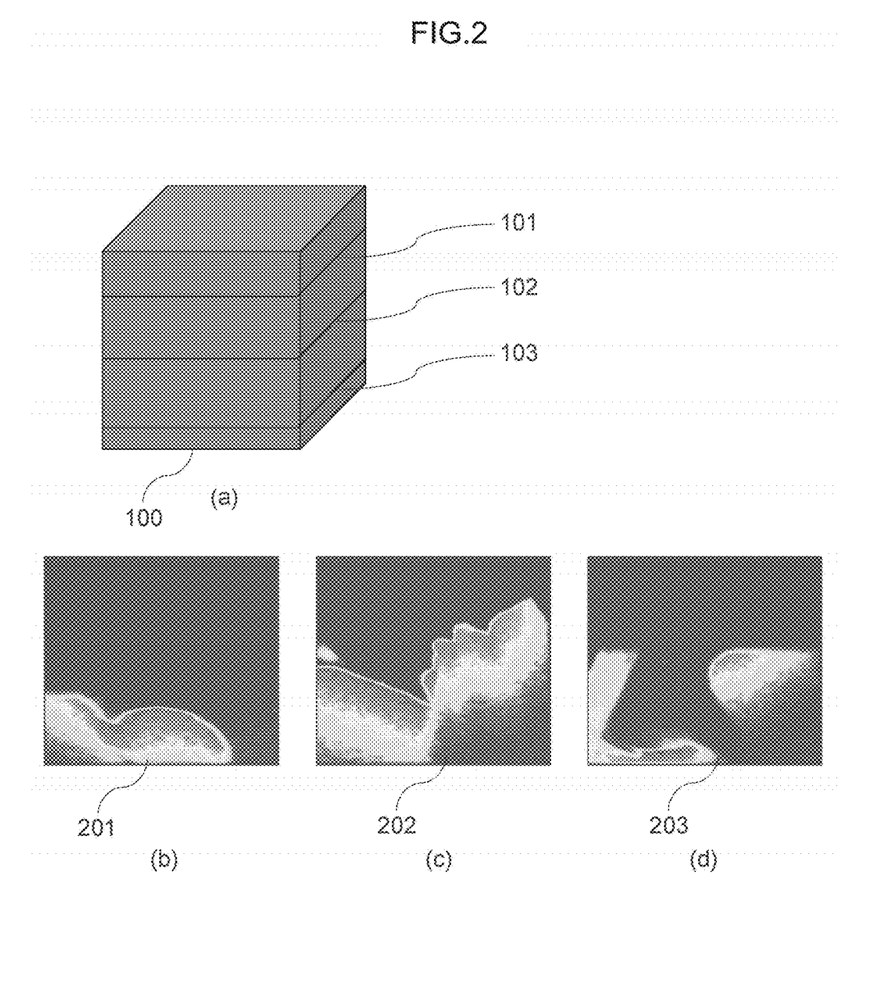
FIG. 2(a) is a schematic diagram of three-dimensional volume data and FIGS. 2(b), 2(c), and 2(d) are configuration diagrams of two-dimensional images acquired from the three-dimensional volume data.

FIG. 2(a) is a schematic diagram of the three-dimensional volume data and FIG. 2(b), FIG. 2(c), and FIG. 2(d) are configuration diagrams of two-dimensional images acquired from the three-dimensional volume data. Referring to FIG. 2, three-dimensional volume data 100 is the three-dimensional volume data generated by the modality 14 and is composed of a voxel value of the cubic three-dimensional arrays. When the cubic three-dimensional volume data 100 is horizontally divided into three parts, volume data 101, 102, 103 are extracted from the three-dimensional volume data 100.

Images 201, 202, 203 shown in FIG. 2(b), FIG. 2(c), and FIG. 2(d) are two-dimensional images respectively acquired from the volume data 101, 102, 103 and show sectional images of the fetus. Specifically speaking, the images 201, 202, 203 correspond to sectional views acquired by horizontally slicing the image of the fetus. Under this circumstance, the images 201, 202, 203 are visualized so that parts with high voxel values become white. Furthermore, the volume data 101, 102, 103 retain quality information about the target, such as information about bones, bloods, etc. as illuminance information. Therefore, the main processor 24 executes processing for detecting the target by determining distribution of the voxel values of the three-dimensional volume data 100.

Figure 3:
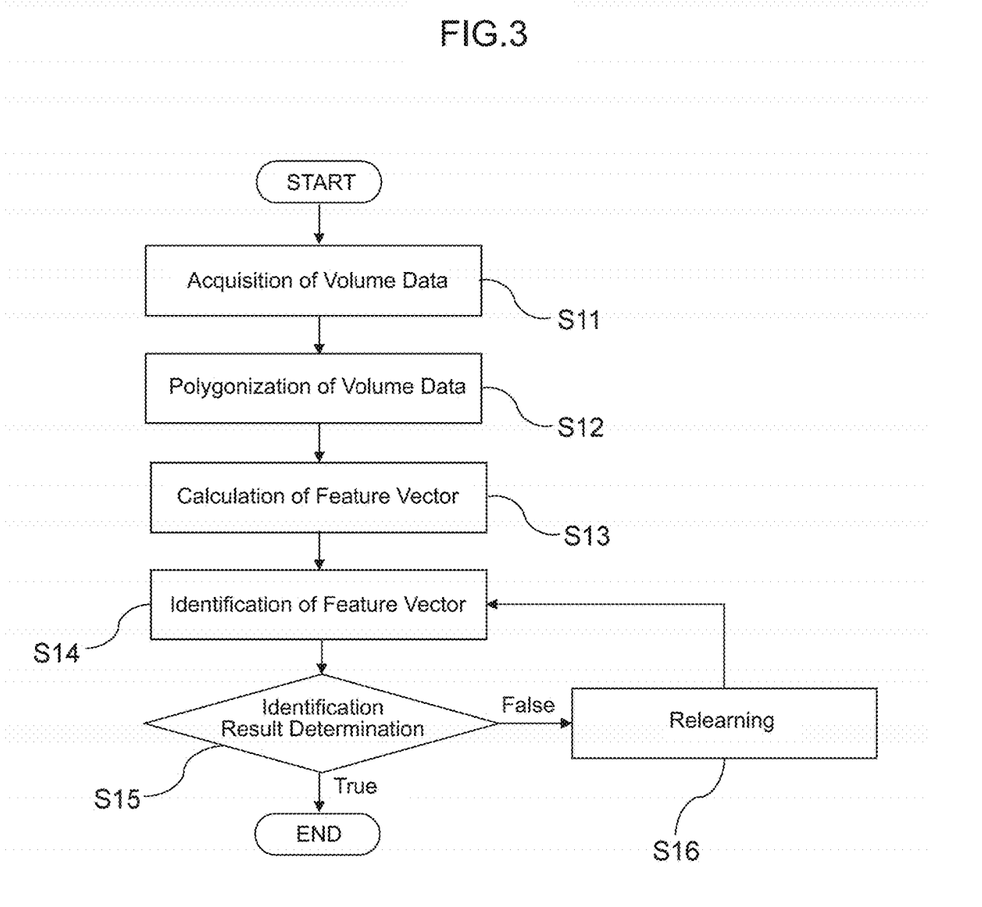
FIG. 3 is a flowchart for explaining processing of a main processor.

FIG. 3 is a flowchart for explaining processing of the main processor. Referring to FIG. 3, the main processor 24 acquires the three-dimensional volume data from the modality 14 (S11), polygonizes and converts the acquired three-dimensional volume data into polygon data, and divides the converted polygon data into a plurality of clusters (S12). Then, the main processor 24 calculates an L2 norm vector of spherical harmonics as a feature vector with respect to each cluster based on the polygon data constituting each cluster (S13), determines whether each cluster is a target or not by comparing each calculated feature vector with learning data (S14), and displays each identification result on the screen of the display 18 and determines each identification result (S15).

Under this circumstance, if the main processor 24 determines that the cluster displayed on the display 18 is the target, that is, if the user determines that the identification result is "TRUE," the main processor 24 terminates the processing in this routine. On the other hand, if the user determines that the cluster displayed on the display 18 is a non-target, that is, the identification result is "FALSE" and is a noise, a tag 403 is attached to the cluster, and the correction information is input from the display 18, the main processor 24 executes relearning processing (S16), then returns to the processing in step S14, and repeats the processing in steps S14 and S15.

Specific details of each step from S11 to S16 will be explained below. Firstly, in step S11, the main processor 24 acquires the three-dimensional volume data from the modality 14 and stores the acquired three-dimensional volume data in the main memory 26.

Next, in step S12, the main processor 24 reads the three-dimensional volume data, which is stored in the main memory 26, to a work area, polygonizes and converts the read three-dimensional volume data into polygon data, and divides the converted polygon data into a plurality of clusters. Under this circumstance, the main processor 24 adopts, for example, a marching cubes algorithm from the viewpoint of reduction of a calculation cost from among methods such as a Delaunay triangulation method and the marching cubes algorithm. In this case, the main processor 24 functions as a cluster generator that polygonizes and converts the three-dimensional volume data, which is generated by the modality 14, into polygon data and divides the converted polygon data into a plurality of clusters.

Incidentally, a polygon is a multiple sided shape composed of a group of three-dimensional vertex coordinates in certain order. Normally, a triangle is used as a polygon among multiple sided shapes constituting polygons. Moreover, a cluster is a group of polygons in which vertexes of the multiple sided shapes (triangles) are coupled to each other. Each cluster is composed of polygon data belonging to polygons of each cluster.

Figure 4:
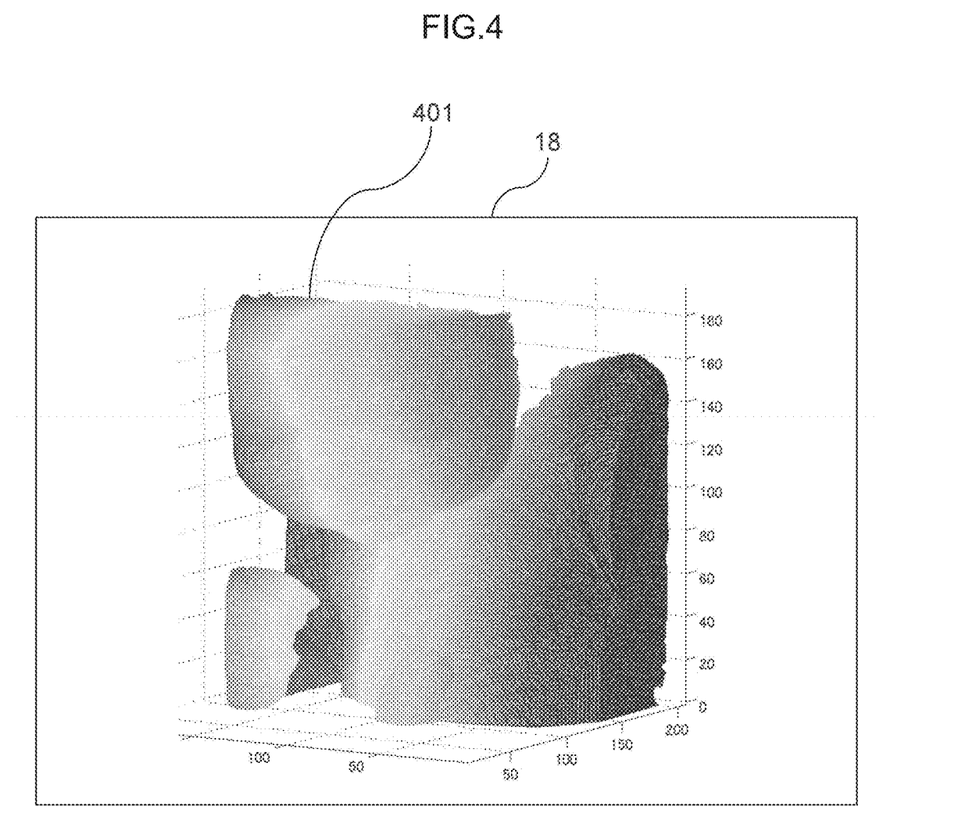
FIG. 4 is a diagram illustrating a display example of an image acquired by polygonizing volume data, that is, a display example of an image of only a target.

FIG. 4 is a diagram illustrating a display example of an image obtained by polygonizing volume data and a display example of an image of only a target. Referring to FIG. 4, the main processor 24 schematically displays a cluster identified as the target, for example, an image of a cluster 401 as a three-dimensional image on the screen of the display 18.

Figure 5:
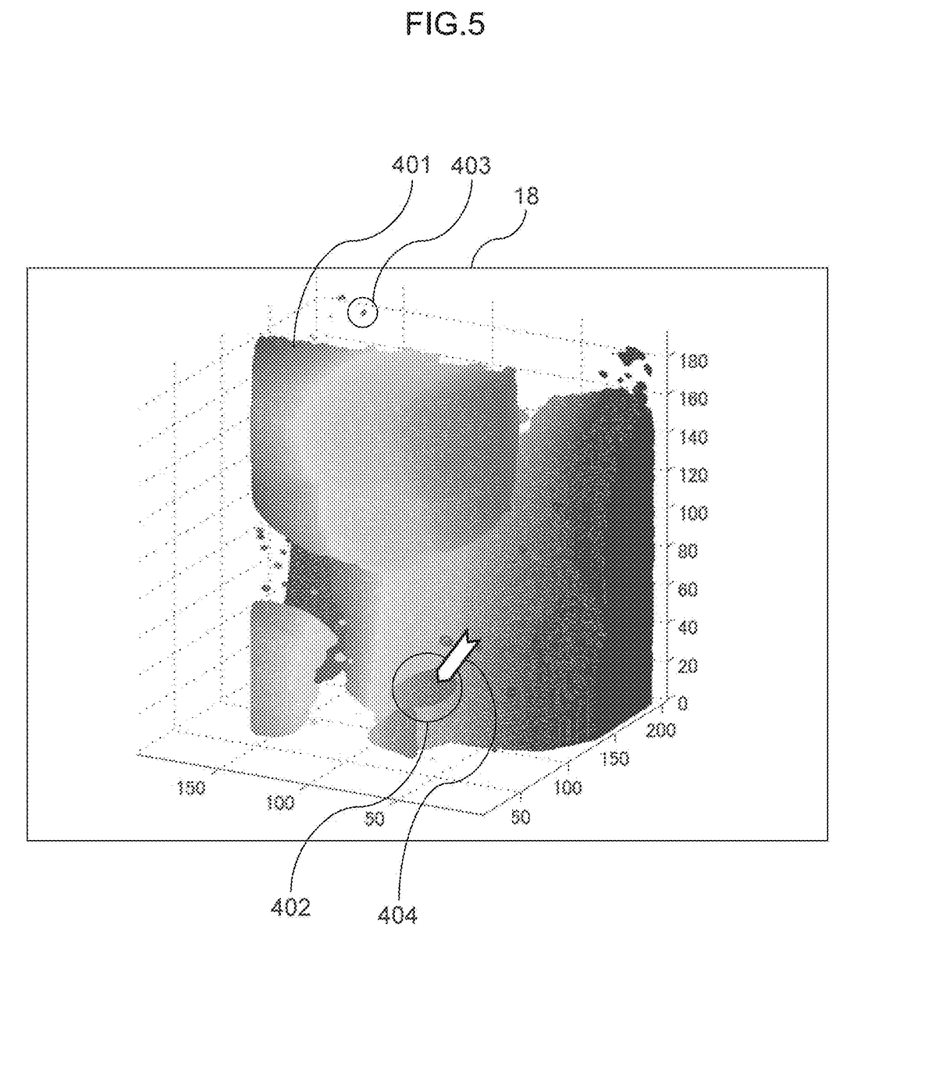
FIG. 5 is a diagram illustrating a display example of an image acquired by polygonizing volume data, that is, a display example of an image including the target and non-targets.

FIG. 5 is a diagram illustrating a display example of an image acquired by polygonizing volume data and a display example of an image including a target and non-targets. Referring to FIG. 5, a cluster identified by the main processor 24 as the target, for example, an image of the cluster 401 is schematically displayed as a three-dimensional image on the screen of the display 18 and clusters which are identified by the main processor 24 as targets, but correspond to non-targets, for example, images of clusters 402, 403 are also schematically displayed as three-dimensional images. Incidentally, in FIGS. 4 and 5, the front side and the back side can be expressed by a cyclic direction of vertexes of each cluster; and in this embodiment, a counterclockwise circuit indicates the front side and a clockwise circuit indicates the back side.

If the images of the clusters 402, 403 are displayed on the display 18 and the user determines that the clusters 402, 403 are images representing noises and are non-targets under the above-described circumstance, the user can perform touch manipulation to add a tag 404, as an identification label for identifying, for example, the cluster 402 as the non-target, to the cluster 402. Information about this tag 404 is input as correction information along with the user's correction manipulation to the main processor 24 via the network processor 20. In this case, the main processor 24 executes relearning processing using a machine learning algorithm based on the input correction information.

Subsequently, in step S13, the main processor 24 calculates a feature vector of each cluster and stores each feature vector obtained by the calculation as one-directional array in the main memory 26. When calculating the feature vector according to this embodiment, a rotation-invariant feature quantity based on spherical harmonics is used; however, identification of higher precision can be performed by using various other feature quantities in combination with the rotation-invariant feature quantity.

Firstly, examples of methods of calculating the feature quantities retained in the feature vectors can include methods of calculating (1) the volume of the cluster, (2) an average value of the volume data included in the cluster, and (3) distribution of the volume data included in the cluster. A further example of the method of calculating the feature quantities retained by the feature vectors can be (4) a method of calculating a histogram of the volume data included in the cluster. When this method is used, the histogram can be added to the feature vector by quantizing voxel values of the volume data included in the cluster into 25 levels.

Furthermore, examples of the method of calculating the feature quantities retained by the feature vectors can include methods of calculating (5) a mean curvature of the polygon data included in the cluster and (6) a Gauss curvature of the polygon data included in the cluster. A further example can be a method of calculating (7) an L2 norm vector, which is a coefficient of the spherical harmonics, from the polygon data of the cluster. When calculating the L2 norm vector, for example, a method of calculating 20-dimensional L2 norm vectors and adding the calculation results to the feature vectors can be used.

When any one of the methods (1) to (7) is used to calculate the feature quantities retained by the feature vectors, the feature vector of one cluster becomes 50-dimensional. When the calculation cost is to be reduced under this circumstance, some of the methods (1) to (7) can be combined and used without using all of them. Under this circumstance, the method (7) of calculating the rotation invariant feature quantity based on the spherical harmonics is used as the basis in combination with any one of the methods (1) to (6) in order to achieve high identification performance in this embodiment.

Incidentally, when clusters are generated by polygonizing the three-dimensional volume data 100 illustrated in FIG. 2 and then 144 clusters exist, the number of feature vectors becomes 145. When the method of polygonizing and converting the volume data into polygon data and calculating the feature vectors by using the converted polygon data is adopted, it is unnecessary to search all pieces of the volume data. So, the calculation cost will be reduced more considerably than the method of calculating the feature vectors directly from the volume data. Incidentally, each dimensional value of the feature vectors varies in a wide range, correction processing is executed. As examples of the correction processing, termination with a fixed number, logarithmic scaling, and so on can be conducted by performing scaling so that the value will become 0 to 1.

A method of calculating the feature quantity from the spherical harmonics by using the method (7) will be explained below.

The spherical harmonics $y_l^m(\omega)$ is determined according to the following formula.

$$y_l^m(\omega) = \begin{cases} \sqrt{2}\, K_l^m \cos(m\phi) P_l^n(\cos\theta) & m > 0 \\ \sqrt{2}\, K_l^m \sin(-m\phi) P_l^{-m}(\cos\theta) & m < 0 \\ K_l^0 P_l^0(\cos(\theta)) & m = 0 \end{cases} \quad \text{[Math. 1]}$$

As for an explanation of the meaning of each parameter in Formula (Math. 1), a normalization coefficient $K_l^m$ is determined according to the following formula.

$$K_l^m = \sqrt{\frac{(2l+1)(l-|m|)!}{4\pi(l+|m|)!}} \quad \text{[Math. 2]}$$

In the above formula, l represents the order of the spherical harmonics, $P_l^m$ represents an Legendre associated function, m represents an integer number which satisfies −l≤m≤l, and ω is expressed by a combination of angles (θ, φ) and is a direction expressed as ω=(sin θ cos φ, sin θ sin φ, cos θ).

Now, one cluster will be taken as an example to explain the method of calculating the feature quantity based on the spherical harmonics.

Figure 6:
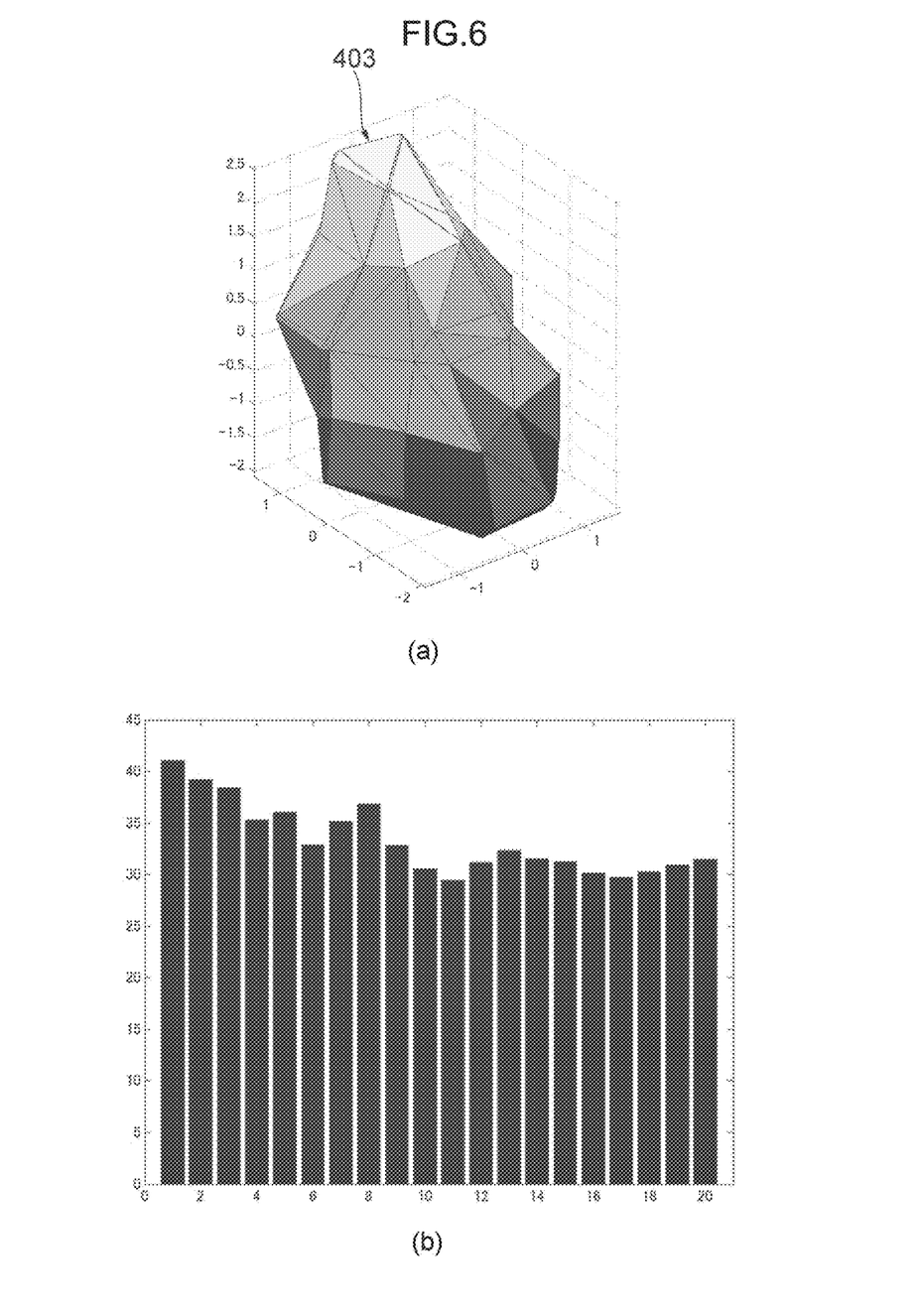
FIG. 6(a) is a diagram illustrating a display example of a three-dimensional image of a cluster identified as a noise and FIG. 6(b) is a diagram that visualizes calculation results, as a histogram, of calculation of an L2 norm vector of N-dimensional spherical harmonics from polygon data of the cluster representing the noise.

FIG. 6(a) is a diagram illustrating a display example of a three-dimensional image of a cluster identified as a noise. Referring to FIG. 6(a), a cluster 403 composed of plurality of polygons is the cluster identified as the noise. When calculating the feature quantity regarding the cluster 403, the main processor 24 executes scaling processing on the cluster 403.

The scaling processing converts three-dimensional coordinate values of polygon data constituting one cluster 403 into a coordinate system, whose origin is set as the center of gravity of the relevant cluster, and then enlarges (or reduces) vertex coordinates of polygons, thereby converting them to a certain size. Upon the scaling processing, adjustments are made to not change an aspect ratio. By executing this scaling processing, it becomes possible to perform stable identification processing regardless of the cluster size. Incidentally, as an example of the scaling processing, this system reduces (or enlarges) the vertex coordinates of polygons so that the long axis (the maximum width of a cluster) becomes 1. After the scaling processing, the following processing is executed.

Regarding coordinate values $(x_i, y_i, z_i)$ of the cluster after the conversion, the directions from the origin are expressed by the following formula.

$$\omega_i = (\sin\theta_i \cos\Phi_i, \sin\theta_i \sin\Phi_i, \cos\theta_i) \quad \text{[Math. 3]}$$

Incidentally, k(k=1, . . . K) represents an index of the coordinate values of the cluster and K represents a total number of vertexes in one cluster. Under this circumstance, an L2 norm vector of N-dimensional spherical harmonics of the index k is expressed by the following formula and is added as a feature quantity obtained by the method (7) to the feature vector.

$$y = \sum_k^K [|y_0(\omega_k)|, |y_1(\omega_k)|, \ldots, |y_n(\omega_k)|, \ldots, |y_N(\omega_k)|]^T \quad \text{[Math. 4]}$$

FIG. 6(b) illustrates an example in which the L2 norm vector of the N-dimensional spherical harmonics is calculated from the polygon data according to Formula (Math. 4) mentioned above and the calculation result is visualized as a histogram.

FIG. 6(b) is a diagram that visualizes, as the histogram, the calculation result of the L2 norm vector of the N-dimensional spherical harmonics from the polygon data of the cluster representing the noise. Referring to FIG. 6(b), each histogram is a histogram acquired from the polygon data of the cluster 403 representing the noise and indicates one-dimensional to 20-dimensional histograms. Incidentally, referring to FIG. 6(b), the horizontal direction indicates the dimension n of the feature vector and the vertical direction indicates the value of the L2 norm of the spherical harmonics.

Figure 7:
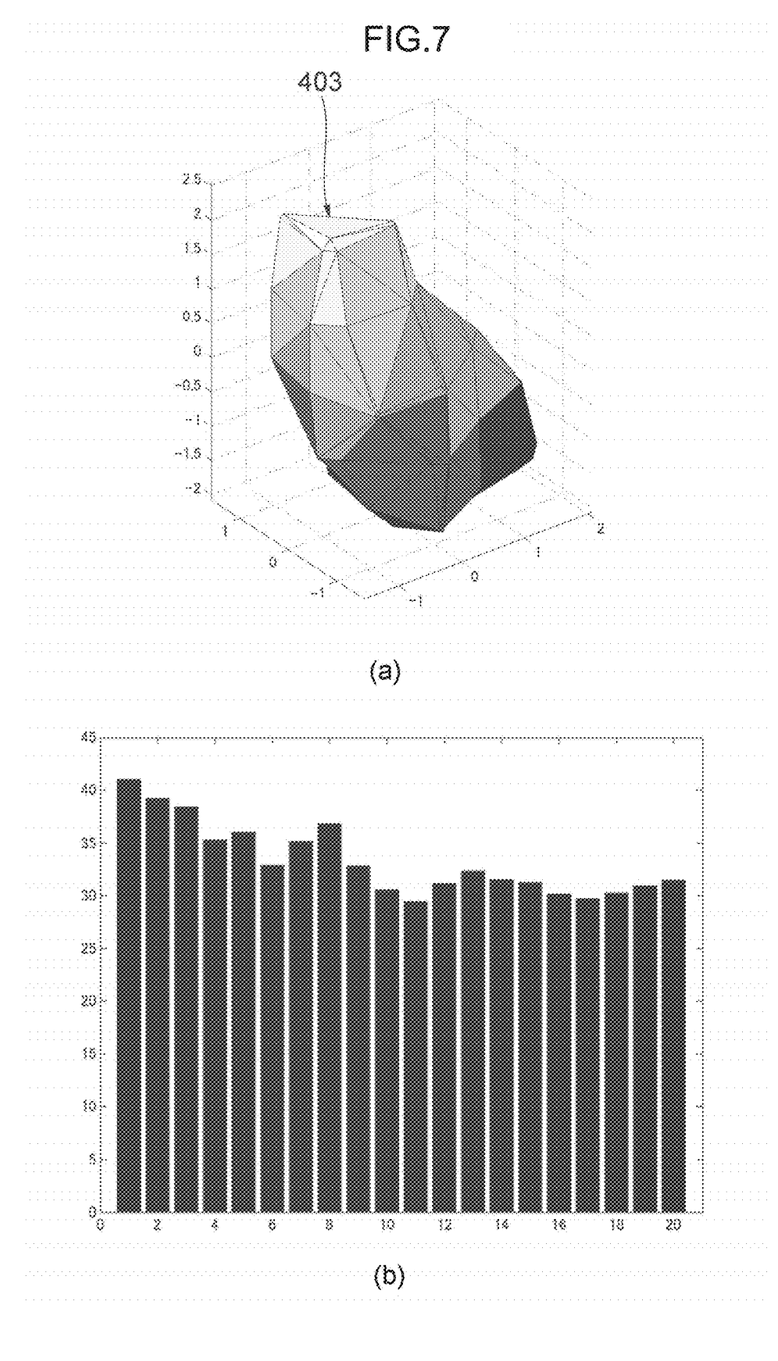
FIG. 7(a) is a diagram illustrating a display example of the three-dimensional image of the cluster, which is acquired by rotating the cluster illustrated in FIG. 6(a) by 90 degrees.
FIG. 7(b) is a diagram illustrating an example that visualizes calculation results, as a histogram, of calculation of an L2 norm vector of N-dimensional spherical harmonics from polygon data of the cluster illustrated in FIG. 7(a)

FIG. 7(a) is a diagram illustrating a display example of a three-dimensional image of the cluster 403 which is obtained by rotating the cluster shown in FIG. 6(a) by 90 degrees.

FIG. 7(b) is a diagram illustrating an example in which the L2 norm vector of the N-dimensional spherical harmonics is calculated from the polygon data of the cluster 403 shown in FIG. 7(a) according to Formula (Math. 4) and the calculation result is visualized as the histogram.

In this embodiment, the L2 norm vector of the N-dimensional spherical harmonics is calculated from the polygon data by using Formula (Math. 4). So, even when the cluster 403 is rotated by 90 degrees, the L2 norm vector of the spherical harmonics calculated from the same cluster 403 becomes the same. Specifically speaking, the value of each dimensional histogram as illustrated in FIG. 6(b) and the value of each dimensional histogram as illustrated in FIG. 7(b) become the same.

Under this circumstance, although it is not precise, the above-described processing is to perform processing for disassembling the cluster 403 into a various shape of spheres and calculating at what rate the various disassembled spheres are included. Under this circumstance, rotary dependency can be eliminated by sequentially adding a dimensional term by using Formula (Math. 4) every time the dimension is increased. Furthermore, disassembly by the spherical harmonics corresponds to, so to speak, Fourier transform using the spheres.

Under this circumstance, the main processor 24 functions as a feature vector calculation unit that calculates the L2 norm vector of the spherical harmonics as the feature vector with respect to each cluster based on the polygon data constituting each cluster.

The method of calculating the feature quantity by combining the marching cubes algorithm with the spherical harmonics has the following advantage.

It is known that polygonization by the marching cubes algorithm has a drawback of generating topological holes. However, if the method of calculating the value of the L2 norm vector of the spherical harmonics of a cluster when calculating the feature quantity retained by the feature vector is used, changes appear between the calculation result regarding clusters with topological holes and the calculation result regarding clusters without topological holes. So, the topological holes can be eliminated more effectively than the case in which other feature quantities are used. Furthermore, when visualization is performed by using the marching cubes algorithm, the relevant data is displayed in a state where the holed clusters are visualized. Therefore, the user can eliminate the holed clusters efficiently.

Next, in step 14, processing for generating identification label data from the feature vector is executed. Under this circumstance, machine learning is used to identify the target based on the feature vector. As a method for this machine learning, for example, a neural network, AdaBoost, and a support vector machine (SVM) can be used. In this embodiment, because of high identification precision and easy explanation, an example of multivalued identification by the SVM (support vector machine) will be explained. Firstly, a definition formula of a single kernel SVM is shown below.

$$L(\alpha) = \sum_{i=1}^{N} \alpha_i - \frac{1}{2} \sum_{i,j}^{N} \alpha_i \alpha_j t_i t_j K(x_i, x_j)$$ [Math. 5]

In the above formula, a represents an optimization variable and t(t∈−1, 1) represents a target value and is a target when t is 1 (t=1). Then, $K(x_i, x_j)$ is a kernel and x represents a feature vector. Incidentally, subscripts i, j of each variable represent indexes of the feature vector and are not dimensions. Regarding Formula (Math. 5) mentioned above, $X_j$, in combination with a feature vector associated with $\alpha_i \neq 0$ (generally called a "support vector") is learning data. It should be noted that generally for identification in machine learning, it is necessary to conduct learning in advance based on training data (a combination of α and x, t).

So, in this embodiment, the main processor 24 executes learning processing in advance by using the SVM (support vector machine) and save the learning result as learning data together with the training data. Incidentally, although Formula (Math. 5) is the single kernel SVM, it is possible to perform identification of higher precision by using a multi-kernel SVM with a plurality of expanded different kernels. Since the identification processing can be executed after conducting learning by changing weights for each dimension k of the feature vector for the multi-kernel SVM, such a method is suited for use of different kinds of feature quantities for the feature vectors.

Figure 8:
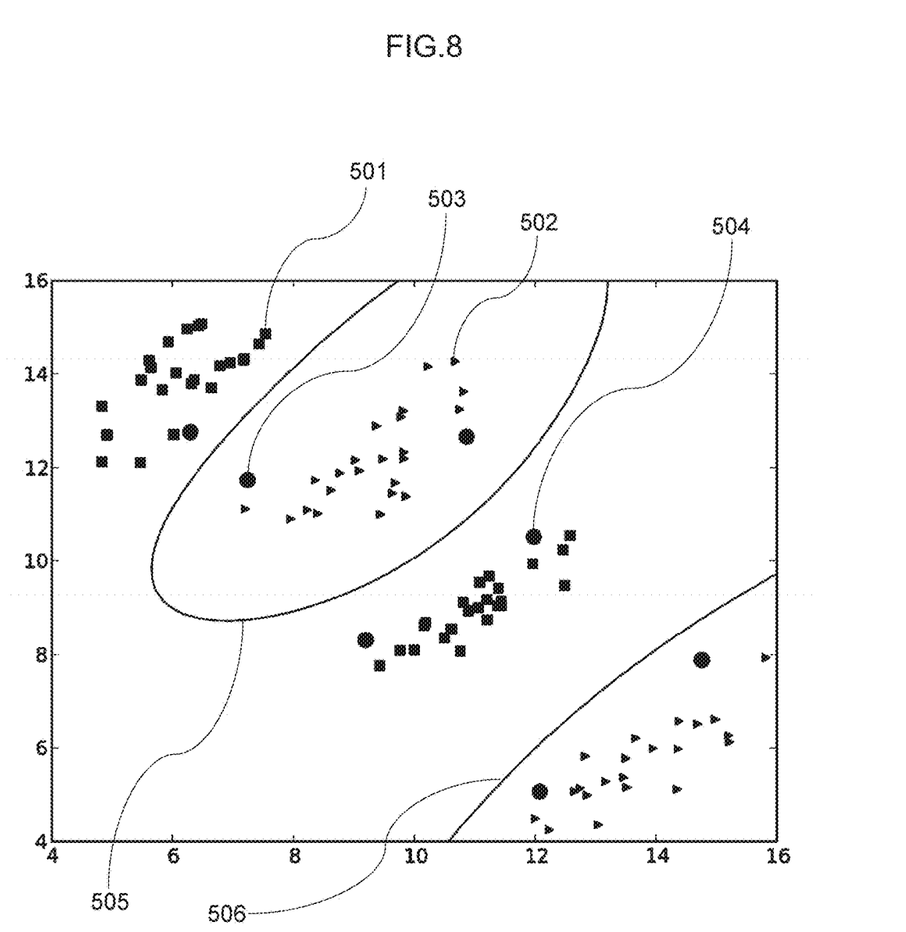
FIG. 8 is a diagram illustrating a display example of an image that visualizes learning results by a support vector machine.

FIG. 8 is a diagram illustrating a display example of an image obtained by visualizing the learning result by the support vector machine. Incidentally, since high-dimensional visualization is not easy, 50-dimensional feature vectors are used in this embodiment and FIG. 8 illustrates an example in which only two dimensions are extracted from the 50 dimensions and an image of the extracted feature vectors is visualized.

A vertical axis in FIG. 8 is one dimension and a horizontal axis in FIG. 8 is another dimension. Referring to FIG. 8, a symbol drawn in a square represents a target 501 and a symbol drawn in a triangle represents a non-target 502. Also, a symbol drawn in a circle represents a training point 503, 504 positioned near a boundary between the target 501 and the non-target 502 and means a support vector. Lines drawn as curved lines are decision surfaces 505, 506 calculated according to the learning data. The decision surfaces 505, 506 are boundaries to identify the target 501 and the non-target 502 and are calculated at such positions that the distance between them becomes maximum with reference to the support vectors (training points 503, 504).

Next, the main processor 24 calculates the following formula based on the learning data and the feature vector of each cluster.

$$y(x_k) = \sum_{i}^{N} a_i t_i K(x_k, x_i) + b$$ [Math. 6]

Incidentally, in Formula (Math. 6), b represents a bias parameter and can be calculated from the learning data. Furthermore, if the value of Formula (Math. 6) is positive, a label indicating the target is given.

For example, if the value of Formula (Math. 6) is positive, that cluster is identified as the target 501; and if the value of Formula (Math. 6) is negative, that cluster is identified as the non-target 502.

If there are a plurality of target types under the above-described circumstance, a method of preparing a plurality of pieces of learning data and solving it as a multi-cluster problem by using a one-to-many method or a one-to-one method. For example, when cluster types are classified into three classes, the main processor 24 can identify clusters as targets or non-targets and can classify the clusters identified as the targets into two types. Under this circumstance, data of a one-dimensional array containing a tuple as an element can be used as label data. Furthermore, regarding labels to be used for identification, for example, a label for class A means a fetus area and a label of class B means a uterus area, and a label meaning a non-target area can be used as a non-target label. Then, data of the labels used for identification are stored as identification label data in the main memory 26.

Next, in step 15, processing for visualizing each cluster based on the identification label data is executed.

Figure 9:
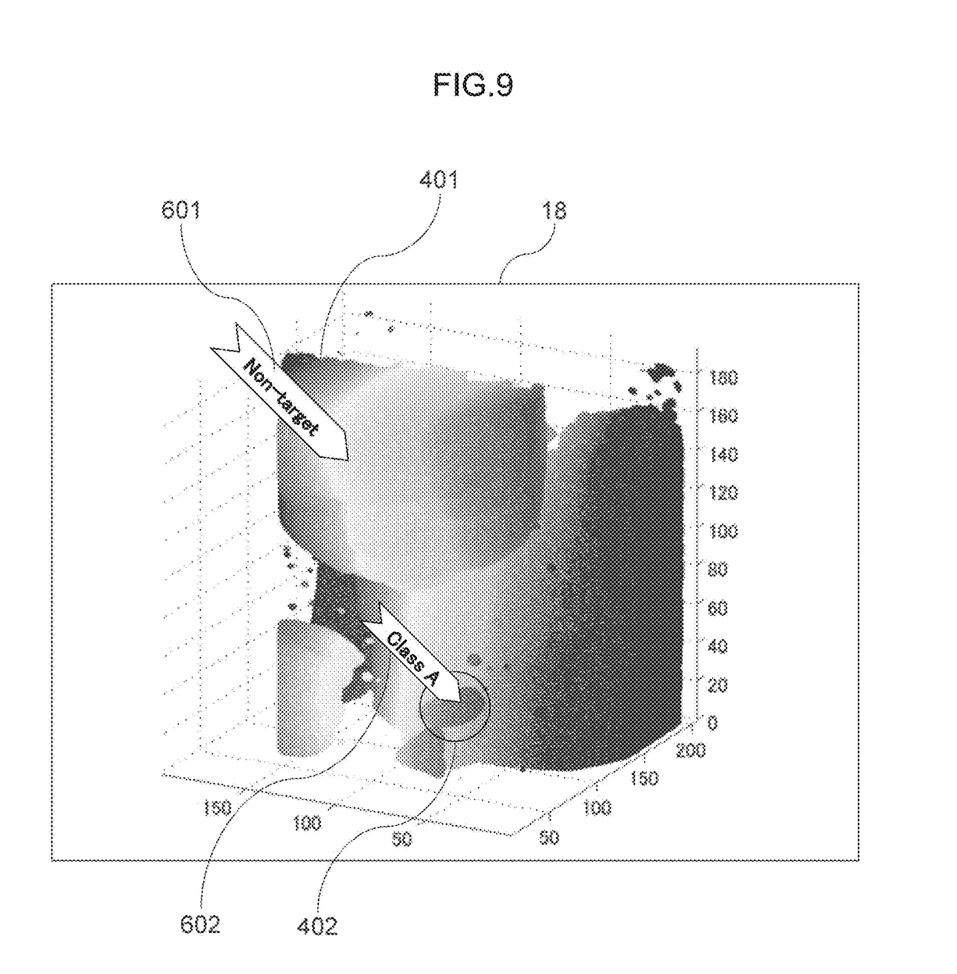
FIG. 9 is a diagram illustrating a display example of a three-dimensional image of clusters to which identification labels are added.

FIG. 9 is a diagram illustrating a display example of a three-dimensional image of clusters to which the identification labels are added. Referring to FIG. 9, a non-target label 601 indicating a non-target is added to the cluster 401 and a target label 402 indicating a target of class A is added to the cluster 402.

When the user determines that the cluster 402 is a noise, correction information to correct the cluster 402 to a non-target can be input by adding a tag 403 by touch panel manipulation of the display 18. Under this circumstance, the main processor 24 displays the target label 602 after correcting it to a non-target label, corrects the label data of the cluster 402 from the label data indicating the target to the label data indicating the non-target, and stores the corrected label data in the main memory 26.

Furthermore, when the user determines that the cluster 401 is a target and the manipulation to correct the non-target label 601 to the target label 602 is executed by means of the touch panel manipulation on the display 18, the main processor 24 corrects the label data of the cluster 401 from the label data indicating the non-target to the label data indicating the target and stores the corrected label data in the main memory 26.

Next, relearning processing is executed in step 16. Under this circumstance, the main processor 24 generates learning data as new learning data by performing relearning of the target based on the corrected label data, the feature vector, and the training data. In this case, the main processor 24 adds the corrected label data and the feature vector to the training data stored at the time of the preliminary learning, optimizes a parameter (optimization variable) based on Formula (Math. 5), stores the learning data obtained after optimization in the main memory 26, and executes the processing in step 14 again.

Under this circumstance, the main processor 24 functions as: a feature vector calculation unit that calculates the L2 norm vector of the spherical harmonics as the feature vector with respect to each cluster based on the polygon data constituting each cluster; an identification unit that identifies whether each cluster is a target or not, based on each feature vector calculated by the feature vector calculation unit and the learning data acquired by machine leaning using the training data; and an image generator that generates an image of a cluster identified as the target by the identification unit, from among respective clusters generated by the cluster generator, from the polygon data constituting each relevant cluster and displays at least the generated image on the display 18.

Furthermore, when the correction information to correct any one of clusters, whose images are displayed on the display 18, is input from the display 18, the main processor 24 functions as: a correction unit that corrects the cluster designated by the input correction information to a target or a non-target; and a relearning unit that relearns the learning data based on the feature vector of the cluster corrected by the correction unit, from among feature vectors calculated by the feature vector calculation unit, and the correction result by the correction unit with respect to the relevant cluster and generates new learning data.

Under this circumstance, when the new learning data is generated by the relearning unit, the main processor 24 also functions as an identification unit that identifies whether the cluster corrected by the correction unit is a target or not, based on the feature vector of the cluster corrected by the correction unit, from among the feature vectors calculated by the feature vector calculation unit, and the new learning data generated by the relearning unit and outputs the identification result to the image generator.

Furthermore, the main processor 24 functions as a correction unit that: corrects the cluster designated by the input correction information to a non-target when the correction information input from the display 18 is the correction information to correct the cluster, whose image is displayed on the display 18, to the non-target; and corrects the cluster designated by the input correction information to a target when the correction information input from the display 18 is the correction information to correct the cluster, whose image is displayed on the display 18, to the target.

Furthermore, when the main processor 24 uses, as the learning data, a plurality of types of learning data according to the type of the target, the main processor 24 functions as: an identification unit that identifies whether each cluster is the target or not, based on the plurality of types of learning data and each feature vector calculated by the feature vector calculation unit and adds label data according to the identification result; and an image generator that has an identification label according to the label data, which is added to the identification result of the identification unit, displayed on the cluster whose image is displayed on the display 18.

According to this embodiment, the volume data is polygonized and the feature vector is found by calculating the spherical harmonics of the polygonized polygon data, so that the calculation cost can be reduced considerably. Also, since only a target area can be detected from the volume data and an image of the detected target can be visualized, false detection will decrease. Furthermore, since the feature quantity of the feature vector does not have rotary dependency, it is possible to achieve both enhancement of detection precision and reduction of the calculation cost. Furthermore, since the calculation cost is low, the result can be acquired at high speed.

Because of the above-described advantageous effects, it is possible to reduce the burdens on the doctors and the engineers and contribute to medical quality improvements.

Incidentally, the present invention is not limited to the aforementioned embodiments, and includes various variations. For example, the aforementioned embodiments have been described in detail in order to explain the invention in an easily comprehensible manner and are not necessarily limited to those having all the configurations explained above. Furthermore, regarding part of the configuration of the embodiment, the configuration of another configuration can be added, deleted, or used for replacement.

Furthermore, part or all of the aforementioned configurations, functions, and so on may be realized by hardware by, for example, designing them in integrated circuits. Also, each of the aforementioned configurations, functions, and so on may be realized by software by processors interpreting and executing programs for realizing each of the functions. Information such as programs, tables, and files for realizing each of the functions may be recorded and retained in memories, storage devices such as hard disks and SSDs (Solid State Drives), or storage media such as IC (Integrated Circuit) cards, SD (Secure Digital) memory cards, and DVDs (Digital Versatile Discs).

REFERENCE SIGNS LIST 10, 12, 14, 16 Modalities; 18 display; 20 network processor; 22 automatic detector; 24 main processor; 26 main memory; 28 auxiliary memory; 30 input device; and 32 output device.

The invention claimed is:
1. A volume data analysis system comprising:
a modality for receiving a measured signal acquired by scanning a measuring object and generating three-dimensional volume data;
an input device for inputting information in response to manipulation;
a controller for processing the three-dimensional volume data generated by the modality and the information input from the input device; and
a display device for displaying a processing result of the controller;
wherein the controller includes:
a cluster generator for polygonizing and converting the three-dimensional volume data generated by the modality into polygon data and dividing the converted polygon data into a plurality of clusters;
a feature vector calculation unit for calculating an L2 norm vector of spherical harmonics as a feature vector with respect to each of the clusters based on the polygon data constituting the each cluster;
an identification unit for identifying whether each cluster is a target or not, based on each feature vector calculated by the feature vector calculation unit and learning data acquired by machine learning by using training data; and
an image generator for generating an image of a cluster identified as the target by the identification unit among each of the clusters generated by the cluster generator, from the polygon data constituting the relevant each cluster and having the display device display at least the generated image.

2. The volume data analysis system according to claim 1, wherein the controller includes:
a correction unit for correcting, when correction information to correct any one of the clusters whose images are displayed on the display device is input from the input device, a cluster designated by the input correction information to a target or a non-target; and
a relearning unit for generating new learning data by relearning the learning data based on the feature vector of the cluster corrected by the correction unit, among the feature vectors calculated by the feature vector calculation unit, and a correction result of the correction unit with respect to that cluster; and
wherein when the new learning data is generated by the relearning unit, the identification unit identifies whether the cluster corrected by the correction unit is the target or not, based on the feature vector of the cluster corrected by the correction unit, among the feature vectors calculated by the feature vector calculation unit, and the new learning data generated by the relearning unit and outputs a result of the identification to the image generator.

3. The volume data analysis system according to claim 1, wherein the identification unit identifies, when a plurality of types of learning data according to a type of the target are used as the learning data, whether each cluster is the target or not based on the plurality of types of learning data and each feature vector calculated by the feature vector calculation unit and adds label data according to the identification result to each identification result; and
wherein the image generator has an identification label according to the label data, which is added to the identification result of the identification unit, displayed on the cluster whose image is displayed on the display device.

4. The volume data analysis system according to claim 1, wherein the cluster generator polygonizes and converts the three-dimensional volume data generated by the modality into the polygon data by either a Delaunay triangulation method or a marching cubes algorithm.

5. The volume data analysis system according to claim 1, wherein the identification unit uses any one of a support vector machine, a multi-support vector machine, AdaBoost, an online support vector machine, or a neural network for the machine learning.

6. A volume data analysis method for a system including:
a modality for receiving a measured signal acquired by scanning a measuring object and generating three-dimensional volume data;
an input device for inputting information in response to manipulation;
a controller for processing the three-dimensional volume data generated by the modality and the information input from the input device; and
a display device for displaying a processing result of the controller;
wherein the controller executes the following steps:
a first step of polygonizing and converting the three-dimensional volume data generated by the modality into polygon data and dividing the converted polygon data into a plurality of clusters;
a second step of calculating an L2 norm vector of spherical harmonics as a feature vector with respect to each of the clusters based on the polygon data constituting each cluster;
a third step of identifying whether each cluster is a target or not, based on each feature vector calculated in the second step and learning data acquired by machine learning by using training data; and
a fourth step of generating an image of a cluster identified as the target in the third step, among each of the clusters generated in the first step, from the polygon data constituting the relevant each cluster and having the display device display at least the generated image.

7. The volume data analysis method according to claim 6, wherein the controller executes:
a fifth step of correcting, when correction information to correct any one of the clusters whose images are displayed on the display device is input from the input device, the cluster designated by the input correction information to a target or a non-target; and
a sixth step of generating new learning data by relearning the learning data based on the feature vector of the cluster corrected in the fifth step, among the feature vectors calculated in the second step, and a correction result with respect to that cluster; and
wherein in the third step, when the new learning data is generated in the sixth step, whether the cluster corrected in the fifth step is the target or not is identified based on the feature vector of the cluster corrected in the fifth step, among the feature vectors calculated in the second step, and the new learning data generated in the sixth step and a result of the identification is reflected in the fourth step.

8. The volume data analysis method according to claim 6, wherein in the third step, when a plurality of types of learning data according to a type of the target are used as the learning data, whether each cluster is the target or not is identified based on the plurality of types of learning data and each feature vector calculated in the second step and label data according to the identification result is added to each identification result; and
wherein in the fourth step, an identification label according to the label data added in the third step is displayed on the cluster whose image is displayed on the display device.

9. The volume data analysis method according to claim 6, wherein in the first step, the three-dimensional volume data generated by the modality is polygonized and converted into the polygon data by either a Delaunay triangulation method or a marching cubes algorithm.

10. The volume data analysis method according to claim 6, wherein in the third step, any one of a support vector machine, a multi-support vector machine, AdaBoost, an online support vector machine, or a neural network is used for the machine learning.

* * * * *